(12) United States Patent
Marsden et al.

(10) Patent No.: US 9,069,390 B2
(45) Date of Patent: Jun. 30, 2015

(54) SYSTEMS AND METHODS FOR MONITORING SURFACE SANITATION

(75) Inventors: Randal J. Marsden, Edmonton (CA); Steve Hole, Edmonton (CA); Daniel Closson, Edmonton (CA)

(73) Assignee: TYPESOFT TECHNOLOGIES, INC., Menlo Park, CA (US)

( * ) Notice: Subject to any disclaimer, the term of this patent is extended or adjusted under 35 U.S.C. 154(b) by 445 days.

(21) Appl. No.: 13/355,450

(22) Filed: Jan. 20, 2012

(65) Prior Publication Data

US 2012/0206384 A1    Aug. 16, 2012

Related U.S. Application Data

(63) Continuation-in-part of application No. 12/234,053, filed on Sep. 19, 2008, now Pat. No. 8,325,141.

(60) Provisional application No. 61/434,772, filed on Jan. 20, 2011.

(51) Int. Cl.
  *G09G 5/00* (2006.01)
  *G06F 3/023* (2006.01)
  *A61L 2/28* (2006.01)

(52) U.S. Cl.
  CPC ............. *G06F 3/023* (2013.01); *G06F 3/0231* (2013.01); *A61L 2/28* (2013.01)

(58) Field of Classification Search
  CPC .......... G06F 3/023; G06F 3/0231; A61L 2/28
  USPC ............................ 345/156–184; 200/5 A, 333
  See application file for complete search history.

(56) References Cited

U.S. PATENT DOCUMENTS

| 4,725,694 A | 2/1988 | Auer et al. |
| 4,805,222 A | 2/1989 | Young et al. |
| 5,404,458 A | 4/1995 | Zetts |

(Continued)

FOREIGN PATENT DOCUMENTS

| CN | 1075222 A | 8/1993 |
| CN | 2662340 Y | 12/2004 |

(Continued)

OTHER PUBLICATIONS

Chen, Capacitive sensing of droplets for microfluidic devices based on thermocapillary actuation, published 2004, available at http://authors.library.caltech.edu/4960/1/CHEIoac04.pdf.*

(Continued)

*Primary Examiner* — Prabodh M Dharia
(74) *Attorney, Agent, or Firm* — Morgan, Lewis & Bockius LLP (57) ABSTRACT

An intelligent touch-sensitive surface that is easy to clean, that self-monitors when it has become contaminated, and can discern when it has been cleaned. The surface incorporates a plurality of sensors that detect events that contribute to contamination and/or cleaning, including, but not limited to, detecting users' touches, movement of the surface, when liquid is present on the surface, when there has been a change of users, time passage since the last cleaning, and how well the surface was wiped. The surface then reports its cleaning status to software residing on a host computer, which in turn can transfer the information to a host server. In this way, the cleaning status of each surface can be monitored remotely and/or logged.

20 Claims, 4 Drawing Sheets

(56) References Cited

U.S. PATENT DOCUMENTS

| | | | |
|---|---|---|---|
| 6,029,578 A * | 2/2000 | Weil et al. | 101/494 |
| 6,396,483 B1 | 5/2002 | Hiller | |
| 6,492,979 B1 | 12/2002 | Kent et al. | |
| 6,504,530 B1 | 1/2003 | Wilson et al. | |
| 6,525,717 B1 | 2/2003 | Tang | |
| 6,563,492 B1 | 5/2003 | Furuya | |
| 6,625,460 B1 | 9/2003 | Patil | |
| 6,650,318 B1 | 11/2003 | Arnon | |
| 6,657,616 B2 | 12/2003 | Sims | |
| 6,707,448 B1 | 3/2004 | Kunimatsu et al. | |
| 6,762,749 B1 | 7/2004 | Gouzman et al. | |
| 7,309,829 B1 | 12/2007 | Ludwig | |
| 7,339,580 B2 | 3/2008 | Westerman et al. | |
| 7,499,039 B2 | 3/2009 | Roberts | |
| 7,554,529 B2 | 6/2009 | Kotipalli | |
| 7,557,312 B2 * | 7/2009 | Clark et al. | 200/5 A |
| 7,659,885 B2 | 2/2010 | Kraus | |
| 7,663,607 B2 | 2/2010 | Hotelling et al. | |
| 7,768,501 B1 | 8/2010 | Maddalozzo, Jr. et al. | |
| 7,813,774 B2 | 10/2010 | Perez-Noguera | |
| 8,019,390 B2 | 9/2011 | Sindhu | |
| 8,350,820 B2 * | 1/2013 | Deslippe et al. | 345/173 |
| 8,390,572 B2 | 3/2013 | Marsden et al. | |
| 8,624,841 B2 | 1/2014 | Kim et al. | |
| 8,716,585 B2 * | 5/2014 | Ludwig | 84/644 |
| 2002/0005108 A1 | 1/2002 | Ludwig | |
| 2002/0005111 A1 | 1/2002 | Ludwig | |
| 2002/0033795 A1 | 3/2002 | Shahoian et al. | |
| 2002/0095586 A1 | 7/2002 | Doyle et al. | |
| 2002/0140667 A1 | 10/2002 | Horiki | |
| 2003/0063073 A1 | 4/2003 | Geaghan et al. | |
| 2003/0071858 A1 | 4/2003 | Morohoshi | |
| 2003/0122784 A1 | 7/2003 | Shkolnikov | |
| 2003/0206162 A1 | 11/2003 | Roberts | |
| 2003/0235452 A1 | 12/2003 | Kraus et al. | |
| 2004/0004559 A1 | 1/2004 | Rast | |
| 2004/0108995 A1 | 6/2004 | Hoshino et al. | |
| 2005/0059418 A1 | 3/2005 | Northcutt | |
| 2005/0063757 A1 | 3/2005 | Sugimura et al. | |
| 2005/0104867 A1 | 5/2005 | Westerman et al. | |
| 2005/0120870 A1 | 6/2005 | Ludwig | |
| 2005/0121980 A1 * | 6/2005 | Bruwer | 307/87 |
| 2005/0122313 A1 | 6/2005 | Ashby | |
| 2005/0162402 A1 | 7/2005 | Watanachote | |
| 2005/0179565 A1 | 8/2005 | Mase et al. | |
| 2005/0190970 A1 | 9/2005 | Griffin | |
| 2005/0246652 A1 * | 11/2005 | Morris | 715/773 |
| 2006/0097991 A1 | 5/2006 | Hotelling et al. | |
| 2006/0152497 A1 | 7/2006 | Rekimoto | |
| 2006/0152499 A1 | 7/2006 | Roberts | |
| 2006/0180450 A1 * | 8/2006 | Clark et al. | 200/333 |
| 2006/0181520 A1 | 8/2006 | Ikegawa | |
| 2006/0192763 A1 | 8/2006 | Ziemkoski | |
| 2006/0232558 A1 | 10/2006 | Chien | |
| 2006/0238503 A1 * | 10/2006 | Smith et al. | 345/156 |
| 2006/0274042 A1 | 12/2006 | Krah et al. | |
| 2006/0274920 A1 | 12/2006 | Tochikubo et al. | |
| 2006/0279548 A1 | 12/2006 | Geaghan | |
| 2006/0284858 A1 | 12/2006 | Rekimoto | |
| 2007/0024593 A1 | 2/2007 | Schroeder | |
| 2007/0047702 A1 | 3/2007 | Newell et al. | |
| 2007/0060131 A1 | 3/2007 | Wilson | |
| 2007/0091070 A1 | 4/2007 | Larsen et al. | |
| 2007/0096930 A1 | 5/2007 | Cardoso | |
| 2007/0120762 A1 | 5/2007 | O'Gorman | |
| 2007/0120832 A1 | 5/2007 | Saarinen et al. | |
| 2007/0139382 A1 | 6/2007 | Kotipalli | |
| 2007/0139395 A1 | 6/2007 | Westerman et al. | |
| 2007/0216658 A1 | 9/2007 | Rainisto | |
| 2007/0229466 A1 | 10/2007 | Peng et al. | |
| 2007/0229476 A1 | 10/2007 | Huh | |
| 2007/0236478 A1 | 10/2007 | Geaghan et al. | |
| 2007/0247316 A1 | 10/2007 | Wildman et al. | |
| 2007/0247429 A1 | 10/2007 | Westerman | |
| 2007/0294263 A1 | 12/2007 | Punj et al. | |
| 2008/0042978 A1 | 2/2008 | Perez-Noguera | |
| 2008/0042989 A1 | 2/2008 | Westerman | |
| 2008/0122796 A1 | 5/2008 | Jobs et al. | |
| 2008/0146082 A1 | 6/2008 | Lin et al. | |
| 2008/0150905 A1 | 6/2008 | Grivna et al. | |
| 2008/0170046 A1 | 7/2008 | Rimon et al. | |
| 2008/0225006 A1 | 9/2008 | Ennadi | |
| 2008/0270558 A1 | 10/2008 | Ma | |
| 2008/0273013 A1 | 11/2008 | Levine et al. | |
| 2008/0281923 A1 | 11/2008 | Barchi | |
| 2008/0289887 A1 | 11/2008 | Flint et al. | |
| 2008/0309519 A1 | 12/2008 | Bengtsson et al. | |
| 2009/0002217 A1 | 1/2009 | Kryze et al. | |
| 2009/0009482 A1 | 1/2009 | McDermid | |
| 2009/0016000 A1 | 1/2009 | Kobayashi | |
| 2009/0045700 A1 | 2/2009 | Sasaki et al. | |
| 2009/0046110 A1 | 2/2009 | Sadler et al. | |
| 2009/0051447 A1 | 2/2009 | McCracken et al. | |
| 2009/0073128 A1 | 3/2009 | Marsden | |
| 2009/0091458 A1 | 4/2009 | Deutsch | |
| 2009/0207574 A1 | 8/2009 | Chen et al. | |
| 2009/0237254 A1 | 9/2009 | Munro et al. | |
| 2009/0237359 A1 | 9/2009 | Kim et al. | |
| 2009/0273477 A1 | 11/2009 | Barnhill | |
| 2009/0273571 A1 | 11/2009 | Bowens | |
| 2009/0282917 A1 | 11/2009 | Acar | |
| 2009/0284476 A1 | 11/2009 | Bull et al. | |
| 2010/0020043 A1 | 1/2010 | Park et al. | |
| 2010/0042827 A1 | 2/2010 | Pratt et al. | |
| 2010/0045705 A1 | 2/2010 | Vertegaal et al. | |
| 2010/0060585 A1 | 3/2010 | Chiu | |
| 2010/0064244 A1 | 3/2010 | Kilpatrick, II et al. | |
| 2010/0065640 A1 | 3/2010 | Maeda et al. | |
| 2010/0085382 A1 | 4/2010 | Lundqvist et al. | |
| 2010/0101921 A1 * | 4/2010 | Howie et al. | 200/61.54 |
| 2010/0153879 A1 | 6/2010 | Rimas-Ribikauskas et al. | |
| 2010/0177057 A1 | 7/2010 | Flint et al. | |
| 2010/0194692 A1 | 8/2010 | Orr et al. | |
| 2010/0323762 A1 | 12/2010 | Sindhu | |
| 2011/0037734 A1 | 2/2011 | Pance et al. | |
| 2011/0043475 A1 | 2/2011 | Rigazio et al. | |
| 2011/0050576 A1 | 3/2011 | Forutanpour et al. | |
| 2011/0068930 A1 | 3/2011 | Wildman et al. | |
| 2011/0126141 A1 | 5/2011 | King et al. | |
| 2011/0227740 A1 | 9/2011 | Wohltjen | |
| 2011/0316703 A1 | 12/2011 | Butler et al. | |
| 2011/0316784 A1 | 12/2011 | Bisutti et al. | |
| 2012/0062382 A1 | 3/2012 | Taneff | |
| 2012/0112906 A1 | 5/2012 | Borke et al. | |
| 2012/0167170 A1 | 6/2012 | Shi et al. | |
| 2013/0187775 A1 * | 7/2013 | Marsden et al. | 340/540 |
| 2015/0049059 A1 * | 2/2015 | Zadesky et al. | 345/174 |

FOREIGN PATENT DOCUMENTS

| | | |
|---|---|---|
| CN | 1864125 A | 11/2006 |
| CN | 101036105 A | 9/2007 |
| CN | 101036205 A | 9/2007 |
| JP | 07-306752 A | 11/1995 |
| JP | 10-208110 | 8/1998 |
| JP | 63311521 A | 12/1998 |
| JP | 11-085352 | 3/1999 |
| JP | 11-136116 | 5/1999 |
| JP | 2002297316 A | 10/2002 |
| JP | 2004265383 A | 9/2004 |
| JP | 2005204251 A | 7/2005 |
| JP | 2005531861 A | 10/2005 |
| JP | 2006323589 A | 11/2006 |
| JP | 2007-184006 A | 7/2007 |
| JP | 2007-184008 A | 7/2007 |
| JP | 2008-544352 A | 12/2008 |
| JP | 2009-520271 A | 5/2009 |
| KR | 200191841 Y1 | 8/2000 |
| KR | 20040106552 A | 12/2004 |
| KR | 20090060888 A | 6/2009 |
| KR | 20090101741 A | 9/2009 |
| KR | 20100029026 A | 3/2010 |
| KR | 20100029421 A | 3/2010 |

(56) References Cited

FOREIGN PATENT DOCUMENTS

| WO | WO 2006/039033 A2 | 4/2006 |
|---|---|---|
| WO | WO 2006/088752 A2 | 8/2006 |
| WO | 2007144014 A1 | 12/2007 |

OTHER PUBLICATIONS

Devlin Medical, CleanKey Keyboard, www.DevlinMedical.co.uk, Hampshire, UK, 1 page, Nov. 6, 2006.
Office Action dated Jul. 12, 2011, received in U.S. Appl. No. 12/234,053, 15 pages.
Office Action dated Nov. 2, 2011, received in Chinese Patent Application No. 200880116618.7, which corresponds to U.S. Appl. No. 12/234,053, 2 pages.
Final Office Action dated Dec. 8, 2011, received in U.S. Appl. No. 12/234,053, 20 pages.
Office Action dated Apr. 24, 2012, received in Chinese Patent Application No. 200880116618.7, which corresponds to U.S. Appl. No. 12/234,053, 7 pages.
Office Action dated Jun. 1, 2012, received in U.S. Appl. No. 12/234,053, 18 pages.
Notice of Allowance dated Sep. 17, 2012, received in U.S. Appl. No. 12/234,053, 7 pages.
Office Action, dated Nov. 8, 2012, received in European Patent Application No. 08 832 204.5, which corresponds to U.S. Appl. No. 12/234,053, 5 pages.
Office Action dated Nov. 16, 2012, received in Chinese Patent Application No. 200880116618.7, which corresponds to U.S. Appl. No. 12/234,053, 7 pages.
Office Action dated Aug. 21, 2012, received in Japanese Patent Application No. 2010-525997, which corresponds to U.S. Appl. No. 12/234,053, 9 pages.
Final Office Action dated Jan. 22, 2013, received in Japanese Patent Application No. 2010-525997, which corresponds to U.S. Appl. No. 12/234,053, 10 pages.
Rejection Decision dated May 9, 2013, received in Chinese Patent Application No. 200880116618.7, which corresponds to U.S. Appl. No. 12/234,053, 6 pages.
Office_Action dated Nov. 26, 2014, received in KR1020107008557, which corresponds to U.S. Appl. No. 12/234,053, 13 pages.
Office Action dated May 19, 2014, received in U.S. Appl. No. 13/442,855, 18 pages.
Final Office Action dated Dec. 9, 2014, received in U.S. Appl. No. 13/442,855, 31 pages.
Notice of Allowance dated Jan. 5, 2015, received in U.S. Appl. No. 13/171,124, 8 pages.
Office Action dated Aug. 26, 2013, received in U.S. Appl. No. 13/171,124, 12 pages.
Office Action dated Feb. 25, 2014, received in Japanese Patent Application No. JP 2013-518583, which corresponds to U.S. Appl. No. 13/171,124, 5 pages.
Final Office Action dated May 29, 2014, received in U.S. Appl. No. 13/171,124, 11 pages.
Office Action dated May 16, 2012, received in U.S. Appl. No. 13/365,719, 20 pages.
Final Office Action dated Oct. 19, 2012, received in U.S. Appl. No. 13/365,719, 9 pages.
Notice of Allowance dated Nov. 13, 2012, received in U.S. Appl. No. 13/365,719, 7 pages.
Office Action dated May 6, 2014, received in U.S. Appl. No. 13/308,416, 19 pages.
Office Action dated Aug. 19, 2014, recevied in Japanese Patent Application No. 2013-542153, which corresponds to U.S. Appl. No. 13/308,416, 5 pages.
Office Action dated Nov. 12, 2014, recevied in Korean Patent Application No. 10-2013-7016964, which corresponds to U.S. Appl. No. 13/308,416, 5 pages.
Final Office Action dated Jan. 30, 2015, received in U.S. Appl. No. 13/308,416, 38 pages.
Final Office Action dated Dec. 22, 2014, received in U.S. Appl. No. 13/308,428, 29 pages.
Office Action dated May 2, 2014, received in U.S. Appl. No. 13/308,428, 12 pages.
Office Action dated May 16, 2014, received in U.S. Appl. No. 13/355,450,12 pages.
Final Office Action dated Nov. 7, 2014, received in U.S. Appl. No. 13/355,450, 22 pages.
Office Action dated Jan. 27, 2014, received in U.S. Appl. No. 13/506,342, 13 pages.
Notice of Allowance dated Nov. 21, 2014, received in U.S. Appl. No. 13/506,342, 8 pages.
Office Action dated Jun. 18, 2013, received in U.S. Appl. No. 13/485,802, 11 pages.
Office Action dated Aug. 10, 2012, received in U.S. Appl. No. 13/485,802, 8 pages.
Final Office Action dated Dec. 10, 2012, received in U.S. Appl. No. 13/485,802, 11 pages.
Office Action dated Feb. 27, 2014, received in U.S. Appl. No. 13/747,469, 8 pages.
Office Action dated Sep. 25, 2014, received in U.S. Appl. No. 14/110,229, 34 pages.
Extended European Search Report, dated Mar. 19, 2012, received in European Patent Application No. 08832204.5, which corresponds to U.S. Appl. No. 12/234,053, 8 pages.
International Preliminary Report on Patentability dated Mar. 24, 2010, received in International Patent Application No. PCT/US2008/077007, which corresponds to U.S. Appl. No. 12/234,053, 4 pages.
International Search Report and Written Opinion dated Apr. 28, 2009, received in International Patent Application No. PCT/US2008/077007, which corresponds to U.S. Appl. No. 12/234,053, 7 pages.
International Preliminary Report on Patentability dated Dec. 28, 2012, received in International Patent Application No. PCT/US2011/042225, which corresponds to U.S. Appl. No. 13/442,855, 4 pages.
International Search Report and Written Opinion dated Feb. 9, 2012, received in International Patent Application No. PCT/US2011/042225, which corresponds to U.S. Appl. No. 13/442,855, 6 pages.
International Preliminary Report on Patentability dated Jun. 4, 2013, received in International Patent Application No. PCT/US2011/062721, which corresponds to U.S. Appl. No. 13/308,416, 5 pages.
International Search Report and Written Opinion dated Jul. 30, 2012, received in International Patent Application No. PCT/US2011/062721, which corresponds to U.S. Appl. No. 13/308,416, 7 pages.
International Preliminary Report on Patentability dated Jun. 4, 2013, received in International Patent Application No. PCT/US2011/062723, which corresponds to U.S. Appl. No. 13/308,428, 5 pages.
International Search Report and Written Opinion dated Jul. 20, 2012, received in International Patent Application No. PCT/US2011/062723, which corresponds to U.S. Appl. No. 13/308,428, 7 pages.
International Preliminary Report on Patentability dated Apr. 1, 2013, received in International Patent Application No. PCT/US2012/000210, which corresponds to U.S. Appl. No. 13/355,450, 7 pages.
International Search Report and Written Opinion dated Jul. 27, 2012, received in International Patent Application No. PCT/US2012/000210, which corresponds to U.S. Appl. No. 13/355,450, 7 pages.
International Preliminary Report on Patentability dated Dec. 2, 2013, received in International Patent Application No. PCT/US2012/040296, which corresponds to U.S. Appl. No. 13/485,802, 5 pages.
International Search Report and Written Opinion dated Jan. 10, 2013, received in International Patent Application No. PCT/US2012/040296, which corresponds to U.S. Appl. No. 13/485,802, 7 pages.
Office Action dated Mar. 12, 2015, received in U.S. Appl. No. 13/71,124, 13 pages. (Marsden).
Notice of Allowance dated Feb. 23, 2015, received in U.S. Appl. No. 13/506,342, 5 pages. (Marsden).

\* cited by examiner

SYSTEMS AND METHODS FOR MONITORING SURFACE SANITATION

PRIORITY CLAIM

This application claims the benefit of U.S. Provisional Application Ser. No. 61/434,772 filed Jan. 20, 2011. This application is also a Continuation-In-Part of U.S. patent application Ser. No. 12/234,053 filed Sep. 19, 2008.

BACKGROUND OF THE INVENTION

With the proliferation of infections in healthcare settings that are difficult to cure, it has become necessary to find ways to clean and disinfect commonly-touched surfaces in order to reduce cross contamination leading to hospital-acquired infections. Hospital-acquired infections result in over 100,000 deaths every year in North America, making it one of the leading causes of death. They also cost the healthcare system in excess of $35 billion dollars annually in caring for patients who have contracted infections in healthcare facilities. To combat these high costs, most healthcare institutions have policies requiring frequent cleaning and disinfection of commonly-touched surfaces, including medical and electronic devices.

But providing cleanable surfaces is only one step in proper infection control protocol. Another important step is that healthcare workers must actually follow the prescribed protocols. Unfortunately, that is not always the case. Many studies have shown compliance to infection-control protocols by healthcare staff, who are often busy and either forget or neglect to follow the proper guidelines, at less than 50%. Other studies have shown a much higher rate of compliance when the process is actively monitored. But it is impractical and expensive to have people monitoring people; a much better approach would be to have the process monitor itself automatically.

The computer keyboard, for example, has been shown to be one of the most contaminated common-touch surfaces in the hospital, with one study showing 62% contamination. Other commonly-touched surfaces have also been identified has highly contaminated in healthcare settings, such as pagers, bed railings, door handles, telephones, counter-tops, faucet handles, TV remote controls, cell phones, and tablet computers. It is important that the surfaces of these objects be easy to clean and disinfect. But it is also very important that compliance to the actions of cleaning and disinfection by healthcare staff be actively monitored and reported on. This can lead to a reduction in the spread of infection in healthcare settings, potentially saving lives and significant healthcare costs.

In U.S. Pat. No. 7,557,312 Clark et al. (hereinafter Clark) describe a keyboard assembly that has a cover making it easy to clean. Clark further describes a sensor and warning system that is operatively coupled to the keyboard assembly that detects when the number of keystrokes and/or time interval has surpassed a certain maximum and warns the user that it is time to clean the keyboard. The sensor assembly then detects when the user has wiped the surface of the keyboard and clears the warning. This approach is useful in that it prompts the user to clean the keyboard (which it might be assumed results in more frequent cleanings) and also attempts to verify that the cleaning has taken place.

There are significant shortcomings however in the approach described by Clark. For example, Clark is specific to a mechanical keyboard with physical keys that travel at least 0.05 inches, making it impossible or impractical to put cleaning sensors on the entire surface of the keyboard. Instead, there are three discrete sensors dispersed over areas of the keyboard where there are no keys. It is a simple matter for a user to identify where these sensors are and fool the system into thinking it has been adequately cleaned by touching only those sensors. The nature of the sensors described (conductive and capacitive) mean a user could simply lick their finger and touch the three sensor areas in order to fool the keyboard into thinking it has been cleaned (the very act of which would in fact make the keyboard more contaminated). A user may be motivated to do this in order to avoid the more laborious task of actually wiping and disinfecting the keyboard.

In U.S. Pat. No. 7,157,655, Murzanski describes a cleanable keyboard in which a barrier layer separates the mechanical keys from underlying electronics, allowing the keys to be cleaned with liquids without the potential of harm to said electronics. In a preferred embodiment, the keyboard may be rinsed under running water without damaging the keyboard circuit. The problem with such a solution in a healthcare setting is that few workers take the time to unplug the keyboard, take it to a sink, and clean it. Further, there is no method included to cue the user when such a cleaning is necessary, nor is there any way to automatically monitor when the cleaning takes place.

SUMMARY OF THE INVENTION

The present invention provides an intelligent touch-sensitive surface that is easy to clean, that self-monitors when it has become contaminated, and can discern when it has been cleaned. The surface incorporates a plurality of sensors that detect events that contribute to contamination and/or cleaning, including, but not limited to, detecting users' touches, movement of the surface, when liquid is present on the surface, when there has been a change of users, time passage since the last cleaning, and how well the surface was wiped. The surface then reports its cleaning status to software residing on a host computer, which in turn can transfer the information to a host server. In this way, the cleaning status of each surface can be monitored remotely and/or logged.

In one embodiment, the surface is configured as a computer keyboard. As described in U.S. patent application Ser. No. 12/234,053 by Marsden, which is hereby incorporated by reference, the surface incorporates touch capacitive sensors as well as vibration sensors to allow the user to rest their fingers on the touch-sensitive surface without selecting. Selections are made by tapping on the surface, as detected by the vibration sensors. These same touch and vibration sensors that are used for detecting the user's touching and selection actions are also used to detect how dirty the surface is, and how well it has been cleaned.

Unlike conventional mechanical keyboards, the present invention can detect not only user selections, but also user touches on the surface (such as resting their fingers). A plurality of touch capacitive sensors are arrayed over the entire surface where they can detect user interaction such as finger resting, sliding, tapping and pressing. This contributes to the determination of surface contamination, since human touch is one of the most significant ways harmful pathogens are spread from surface to surface.

The same touch capacitive sensors described above can also detect when the user has wiped the surface, whether or not it was wiped with a liquid, and what type of liquid was used. Marsden describes an exemplary method for detecting a wiping motion. In one aspect of the invention, detection of a wiping motion automatically suspends operation of the device incorporating the touch surface, allowing it to be cleaned.

When the surface is dry, the capacitive sensors register a normative or "baseline" value over the entire surface. When liquid is present on the touch surface, the value registered by the touch capacitance sensors is different than the baseline value. Thus, after a wiping motion is detected, the system compares the touch capacitance values with those prior to wiping and can tell if liquid was left behind as a result of the wiping action. This ensures that a user can't try to "fool" the system by simply performing a wiping motion with their hand over the surface without using cleanser (in which case they would actually be making the surface more contaminated).

When the surface is wiped using a liquid, the moisture affects the capacitance of most of the surface uniformly. If, for example, a user has wet fingers, only the areas they touch will be affected by the moisture while the rest of the surface that remains dry will not. This information is used to determine the difference between touching with wet fingers and the surface being wiped with a liquid.

As the liquid on the touch surface dries, the capacitance values return to their original baseline state. The evaporation rate varies from liquid to liquid; for example, an alcohol-based cleaner will evaporate much quicker than water. The system monitors the rate of change of the capacitance sensors as the liquid dries and thus is able to estimate what type of liquid is on the surface. This is helpful in determining whether or not a disinfecting cleanser was used as opposed to just water. A manual calibration procedure may be followed to measure the evaporation rate of specific fluids in specific environments, the results of which are stored in a database for reference by the system.

Because the touch capacitive sensors are arrayed over the entire surface, they can also be used to determine where the user has wiped. This information is fed back to the user, for example, as a virtual image of the touch surface device on display attached to the touch surface or the display of a computer wherein the color of the virtual surface changes as the real surface is wiped. In an alternative embodiment, an illumination component is configured to illuminate the touch surface at one of a various of colors or intensity. In this way, the user has immediate visual feedback ensuring they have wiped the surface adequately. The system may also incorporate the wipe coverage data into a policy-based rule set to determine when the user has wiped the surface well enough to clear any cleaning alerts that the system may have issued.

The surface of the present invention also incorporates accelerometers to detect vibrations and movement. These sensors are primarily used to determine when the user taps on a location of the touch surface to indicate a selection. The accelerometers (or other forms of motion/vibration sensors) can also be used to determine when surface has been moved; a contributing factor to cross-contamination. Motion information is stored by the system and used in collaboration with data from other sensors to determine when the potential contamination of the surface exceeds maximums defined by policies set by the institution.

In one aspect of the invention, proximity sensors are used in the touch surface to determine when a human is near the device incorporating the touch surface. As activity around the device increases, so does the probability of contamination. This data can thus be used to contribute to a contamination "score" along with other input described herein.

In yet another aspect of the invention, the system determines when there has been a change of user of the device. It does so using a plethora of data from the sensors described herein including, but not limited to, the touch "signatures" of the users fingers, the strength by which they tap on the surface, whether or not they rest their fingers and on what parts of the surface, and the speed at which they make selections. When the system detects a change of user, it increases the contamination score accordingly.

Embodiments implementing the cleanable surface described herein can encompass a variety of devices, such as universal infrared remote controls, keyboards, computer mice, pagers, tablet computers, telephones, keypads, door knobs, drawer handles, countertops, bed railings, smartphones, and input surfaces on specialized medical equipment. These "smart surfaces" can also report to a monitoring agent and monitoring service in the manner illustrated in FIG. 1B.

This summary is provided to introduce a selection of concepts that are further described below in the detailed description. This summary is not intended to limit the scope of the claimed subject matter.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

The present invention describes methods and systems that electronically monitor and log the contamination status and cleaning status of a cleanable touch surface. This is made possible by sensors that are incorporated into the surface including, but not limited to, capacitive touch sensors, which can be employed to detect when the surface has been cleaned (and how well it has been cleaned).

Figure 1:
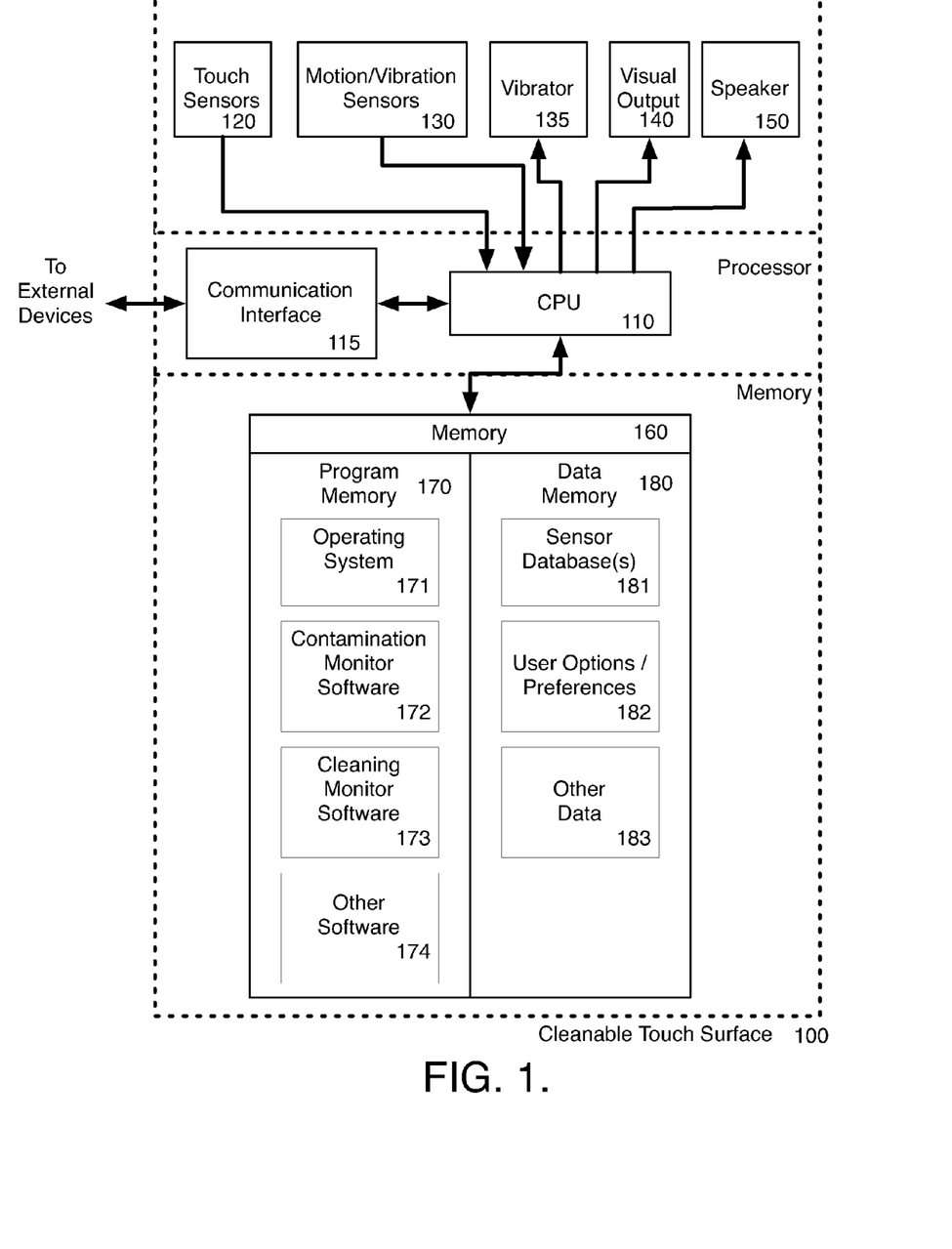
FIG. 1 is a hardware block diagram showing the typical hardware components of a system which embodies the present invention of a cleanable touch surface.

FIG. 1 shows a simplified block diagram of the hardware components of a typical device 100 in which the System and Method for a cleanable touch surface is implemented. The device 100 includes one or more touch sensors 120 that provides input to the CPU (processor) 110 notifying it of contact events when the surface is touched, typically mediated by a hardware controller that interprets the raw signals received from the touch sensor(s) and communicates the information to the CPU 110 using a known communication protocol via an available data port. Similarly, the device 100 includes one or more motion (or vibration) sensors 130 that communicate with the CPU 110 when the surface is tapped, in a manner similar to that of the touch sensor(s) 120. The CPU 110 communicates with a hardware controller for a visual output 140 to send user alerts. A speaker 150 is also coupled to the CPU 110 so that any appropriate auditory signals can be passed on to the user as guidance. A vibrator 135 is also coupled to the CPU 110 to provide appropriate haptic feedback to the user. The CPU 110 has access to a memory 160, which may include a combination of temporary and/or permanent storage, and both read-only and writable memory (random access memory or RAM), read-only memory (ROM), writable non-volatile memory such as FLASH memory, hard drives, floppy disks, and so forth. The memory 160 includes program memory 170 that contains all programs and software such as an operating system 171, contamination monitor software 172, cleaning monitor software 173, and any other application programs 174. The memory 160 also includes data memory 180 that includes a sensor database(s) 181 required by the contamination monitor software 172 and the cleaning monitor software 173, storage for maintaining a record of user options and preferences 182, and any other data 183 required by any element of the device 100. The CPU 110 may send information related to the contamination levels and cleaning status of the cleanable touch surface 100 to external devices or controllers by communicating through a standard communication interface 115.

Figure 2A:
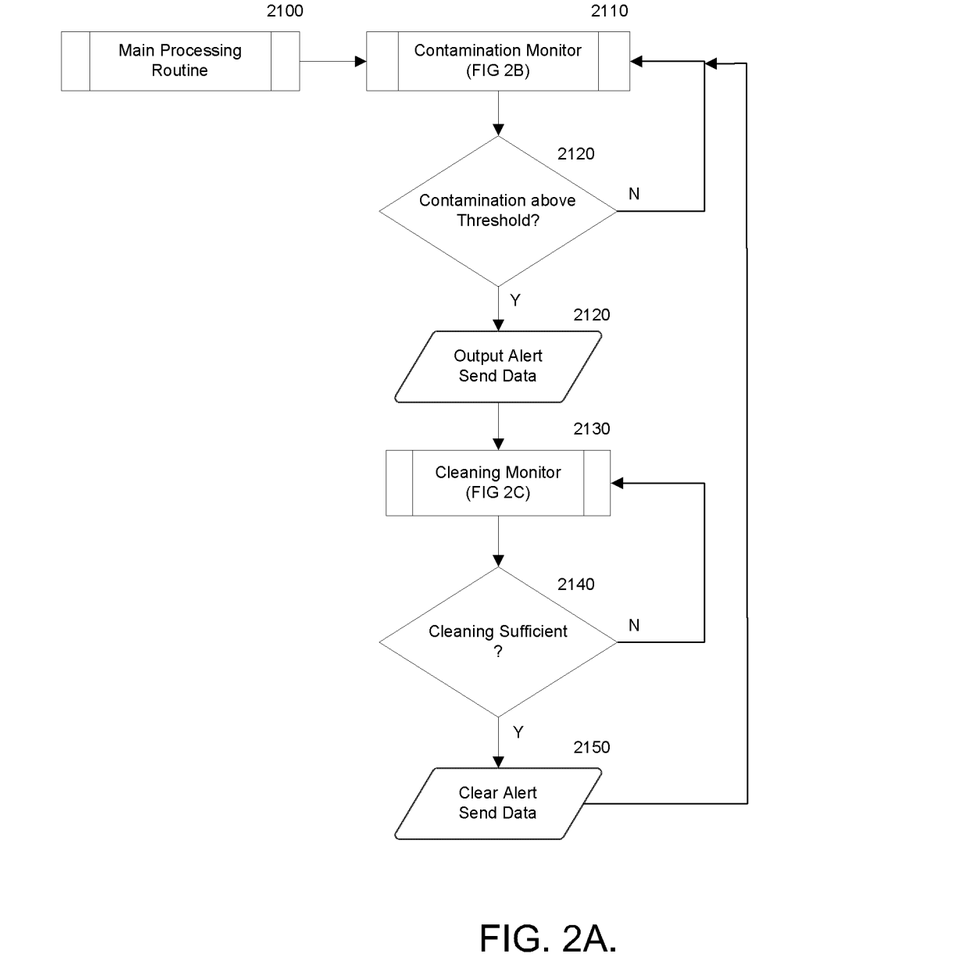
FIGS. 2A through 2C show a flow diagram of an exemplary process performed by the system shown in FIG. 1.
Figure 2B:
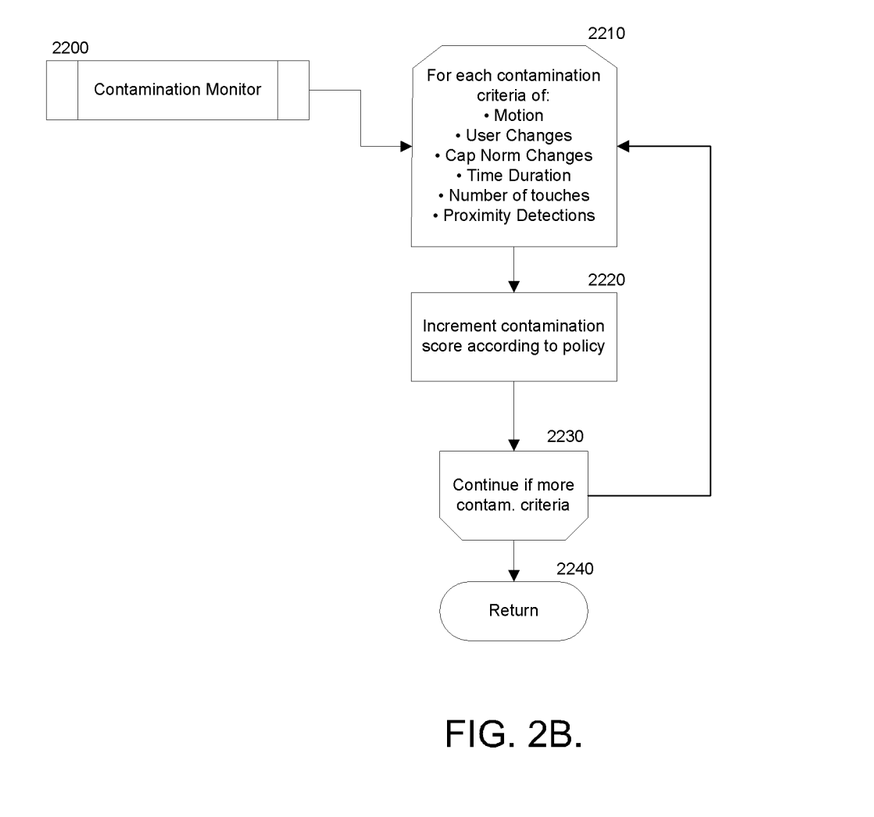
Figure 2C:
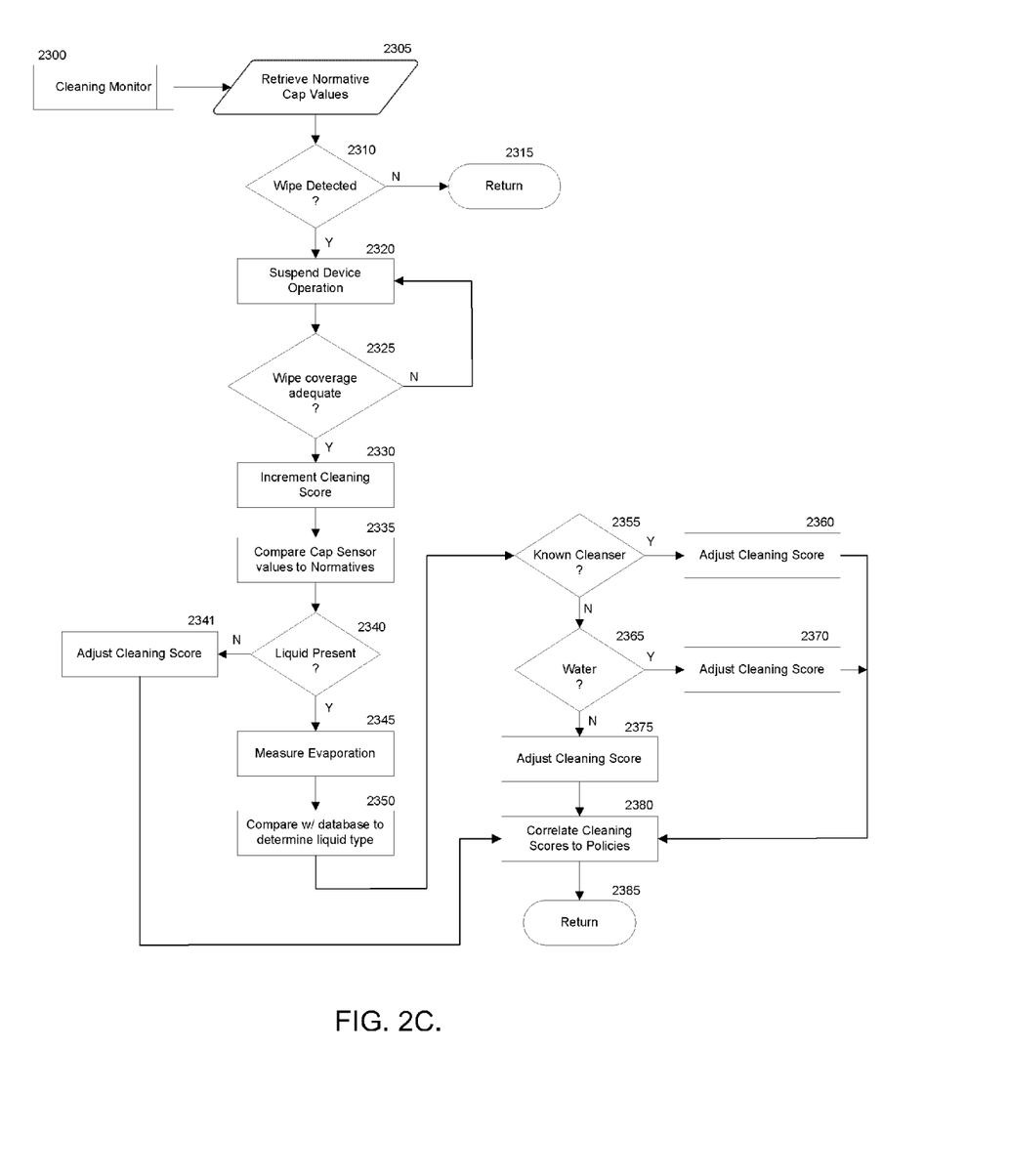

FIGS. 2A through 2C show a process flow chart of an exemplary process performed by the contamination monitor software 172 and the cleaning monitor software 173. The flowcharts shown in FIGS. 2A to 2C are not intended to fully detail the software of the present invention in its entirety, but are used for illustrative purposes.

FIG. 2A shows a flow chart of the Main Processing Routine 2100 performed by the contamination monitor software 172 and the cleaning monitor software 173. At block 2110 the process invokes a Contamination Monitor sub-routine (FIG. 2B) to determine the level of contamination on the surface. At block 2120 the system determines whether or not the contamination level exceeds a specified threshold. This threshold is a user-changeable variable that is typically defined via a software control panel or through a user interface provided by the device 100 and stored in user preference memory 182. If the contamination level has not exceeded the defined threshold, the process returns back to block 2110 to continue monitoring for contamination.

If the contamination threshold has been exceeded, the process moves to block 2120 where it outputs an alert according to administrator-defined policy. The alert can take many forms including, but not limited to: visual indicator displayed on the visual output 140 (e.g., display device or device configured to illuminate the touch surface) of the device 100, an audible alert output on the speaker 150, a haptic alert output by the vibrator 135, or data that is sent via the communication interface 115 to external monitoring devices or software.

After issuing an alert, the process moves to block 2130 (FIG. 2C) where it monitors for cleaning actions taken. In block 2140, the system decides whether or not cleaning has been sufficient. What is deemed sufficient by the cleaning monitor software 173 is defined by an administrator and stored as a user preference in the memory 182. If cleaning has not been sufficient, the process returns to block 2130 to continue monitoring for cleaning activities. If the cleaning is sufficient, the process moves to block 2150 where the alert is cleared (or stopped). The process then returns to the start and once again begins monitoring for contamination in block 2110.

FIG. 2B shows a flowchart of an exemplary process for determining the contamination levels. The routine begins at block 2200 and continues for each contamination criteria in block 2210. There are many factors determined by the CPU 110 based on sensor and/or other data that can contribute to the cleanable surface becoming contaminated. By way of example, these might include: how often the device incorporating the cleanable surface has been moved, the number of times a different user has used the device, changes to the normative values of the touch sensors, a passage of time, the number of times the surface has been touched, and the number of times a human was detected within the proximity of the device. This list is not intended to be exhaustive and it will be evident to anyone skilled in the art that other criterion for determining contamination exists. Each contamination criteria examined in block 2210 will contribute to a contamination score in block 2220 and the process repeats for each criteria in block 2230. Once all contamination criteria have been examined, the process returns with a contamination score at block 2240.

FIG. 2C shows a flowchart of an exemplary process for determining the cleaning levels of the touch surface. The routine begins at block 2300 and retrieves the stored baseline value(s) for the touch capacitive sensors. These are the normative signal levels registered by the sensors when they are dry and not being touched. In one embodiment, the CPU 110 dynamically updates these normative values over time, to adapt to any changes in environment, signal degradation, or other factors which may affect the sensor's signal. Touch capacitive sensors are particularly useful in this application since the signal registered by each sensor differs if the surface is wet or dry. Thus, they can be used to detect the presence of liquid. When the surface is wiped using a liquid, the moisture effects the capacitance of the surface uniformly. This provides a second means whereby the adequacy of the cleaning of the surface can be determined (in addition to wipe detection). If, for example, a user has wet fingers, only the areas they touch on the surface will be affected by the moisture while other areas that remain dry will not. This information can easily be used to determine the difference between touching with wet fingers and the surface being wiped uniformly with a liquid.

The system then watches for a wiping motion in block 2310. In one embodiment, the CPU 110 determines when the surface has been cleaned by a wiping action.

Wipe detection is particularly useful when a user initiates cleaning the surface but has forgotten to pause it first. If the system detects touches that are indicative of a wiping action, it can automatically suspend or pause the operation of the device. In one embodiment, the device has an explicit method for the user to select pause mode, which disables functionality to allow the surface to be cleaned. A user may forget or choose not to activate this mode before cleaning. To accommodate this circumstance, the CPU 110 detects a wiping motion as a moving cluster of adjacent touches occurring simultaneously. As that cluster of touches begins to move, the CPU 110 determines the action to be a wiping motion and functionality of the device is temporarily disabled, allowing the wiping motion to take place without the pause mode being manually activated.

If a wiping motion is not detected, the process exits at block 2315. If a wiping motion is detected, the system suspends operation of the device in block 2320. In block 2325 the CPU 110 determines if wipe coverage was adequate. For example, if only half of the touch surface was wiped, the CPU 110 automatically ascertains this and judges this wiping action to be an incomplete wipe.

In infection sensitive environments, the contamination on the surface may not be visible to the naked human eye. In fact, the most harmful pathogens are almost always invisible. In this circumstance, the user doesn't have the benefit of seeing where they have or haven't wiped by simply looking at the presence or absence of contamination. Further, many cleaning liquids are clear again making it difficult for a user to know if they have cleaned the entire surface adequately.

To assist with this problem, an embodiment of the cleanable surface incorporates a virtual visual representation of the surface on a display (either attached to the surface or on the screen of a connected computer (the visual output 140)). This visual representation, sometimes referred to as a "heat map", changes the color of the virtual surface (or touch surface) wherever a touch occurs. Over time, the more the surface is touched, the more the virtual surface (or touch surface) becomes colored. As the user wipes the cleanable surface, the virtual surface representation provides feedback whereby the colorization is removed corresponding to where the wiping takes place. In effect, the user "erases" the coloring on the virtual surface by wiping the real surface. In this way, they are provided immediate visual feedback as to the adequacy of their wiping action.

Once the CPU 110 determines the wiping coverage is adequate, it increments a cleaning "score" in block 2330. The process continues to block 2335 where the CPU 110 compares the capacitive sensor values right after the wipe is completed with the baseline values retrieved in block 2305. A uniform difference between all the sensors as determined by the CPU 110 indicates the presence of a liquid on the surface as determined in block 2340. If no liquid is found to be present, the process adjusts the cleaning score accordingly in block 2341 and then proceeds to block 2380 where the cleaning score is compared with stored policy data. Policy data is typically defined by a facility administrator in which the device is being used. For example, a hospital may choose to have a policy that the surface must be cleaned with a liquid. If no liquid was used then the process would determine that the cleaning was not adequate. The policy data may reside onboard the device 100 in the data memory 182, or it may be stored external to the device and communicated via the communication interface 115

If liquid is detected in block 2340 the process moves to block 2345 where the CPU 110 measures the rate of evaporation of the liquid from the cleanable touch surface. It does this in an effort to determine the type of liquid used to clean the surface. Some policies, for example, may dictate that a certain type of cleanser or disinfectant be used while others may allow only water. The CPU 110 ascertains, to the extent possible, what type of liquid was used during the wiping action.

In one embodiment, the CPU 110 uses data from the capacitive sensors in the surface to determine the presence of moisture on the surface. Moisture changes the capacitance of the surface, and can therefore be detected using the touch capacitive sensors in the surface.

Further, as the liquid evaporates from the surface, the capacitance on the surface changes accordingly and can be detected by a change in capacitance of the surface's capacitive touch sensors. By measuring this change, the rate of evaporation is determined and correlated to various known cleaning liquids (such as water and alcohol). For example, the evaporation rate of alcohol is faster than that of water, and so the surface can tell the difference between water and alcohol. Thus, using the evaporation rates of the cleaning liquid, the CPU 110 can determine what type of liquid was used to clean its surface. The rate at which a liquid evaporates is stored as "evaporation signatures" in the data memory sensor database 181.

The rate of evaporation can vary even for the same liquid from environment to environment. For example, most liquids will evaporate slower in a humid, cool environment than they will in a dry, hot environment. To accommodate for this variability, an embodiment of the present invention allows the user to calibrate the surface for the liquid being used and the environment in which it is being used. They do this by putting the device into a "learn" mode and then coat the surface with the liquid. The system then records the rate of evaporation of that liquid in that environment and stores it in the sensor database 1081 for reference in block 2350 of FIG. 2C.

In another embodiment, a local humidity value is retrieved from a local or remote (e.g., website) source via the communication interface 115. The retrieved humidity value is then used by the CPU 110 to alter the stored evaporation rates.

The process determines whether or not the liquid is a known cleanser in block 2355 of FIG. 2C. If it is a known cleanser, it adjusts the cleaning score accordingly in clock 2360. If it is not a known cleanser then the CPU 110 determines if the liquid was water in block 2365, and then adjusts the score accordingly in block 2370 (for water) and block 2375 for not water. In the case of block 2375, it is an unknown liquid and a flag or warning can be issued prompting the user to identify the liquid and/or carry out a calibration so the CPU 110 can store the evaporation signature of the new liquid.

The process continues to block 2380 where the cleaning score is compared with policies stored in user preferences data 182, or alternatively retrieves the policy data from an external device via the communication interface 115. It should be noted that the term "cleaning score" is used simply for illustrative purposes, and that in reality a more complex set of rules make up the algorithm that determines whether or not the cleaning has been adequate and meets the requirements of the stored policies. The process then exits at block 2385.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A system comprising:
    a touch surface having a plurality of sensors to generate one or more signals in response to contact with the touch surface; and
    a processing device, in signal communication with the plurality of sensors, to interpret a first contact indicated, at least in part, by a first signal generated by a first one of the sensors as an activation of a user-selected key on a keyboard, and to interpret a second contact as a wiping motion indicated, at least in part, by a second signal generated by the first one of the sensors as a cleaning action with respect to the touch surface, wherein the processing device is configured to suspend operation of the keyboard during the cleaning action.

2. The system of claim 1, wherein the processing device determines whether the touch surface has reached a contaminated state based on one or more of the following events: whether the one or more signals are identified by the processing device as human touches and the identified human touches exceed a predefined threshold; whether the processing device determines that a user of the touch surface is different from a previous user of the touch surface; whether the processing device determines the touch surface has moved more than a predefined amount based on one or more received motion signals; whether the processing device determines that time since a previous cleaning event exceeds a predefined time threshold; whether the processing device determines a proximity event has occurred based on a received proximity detection signal; or whether the processing device determines that baseline readings of the one or more signals exceeds a predefined threshold.

3. The system of claim 1, wherein the processing device determines a contamination level of the touch surface based at least in part on the one or more signals generated by the plurality of sensors, the system further comprising an illumination component to illuminate the touch surface in at least one of a time-varying color or a time-varying intensity according to the contamination level of the touch surface.

4. The system of claim 1, further comprising at least one of a display device, integrated with the touch surface and in signal communication with the processing device, wherein the processing device is further configured to issue an alert when the touch surface has been determined to reach a contaminated state, wherein the alert comprises at least one of a visual alert outputted by the display device, an audible alert outputted by the speaker or a tactile alert outputted by the tactile feedback device.

5. The system of claim 1, wherein the processing device is further to suspend functional operation of the touch surface when the touch surface has been determined to reach a contaminated state.

6. The system of claim 1, further comprising a display device disposed visibly beneath the touch surface and coupled to the processing device, wherein the processing device is further to render a keyboard image on the display device and to determine a time-varying contamination level based on the one or more signals generated by the plurality of sensors and to visibly alter the keyboard image over time in accordance with the time-varying contamination level.

7. The system of claim 1, wherein the processing device to interpret the first contact as an activation of a user-selected key and to interpret the second contact as a cleaning action with respect to the touch surface comprises a programmed processor to determine, based at least in part on the first signal, that a keystroke has occurred with respect to the user-selected key, and to determine, based at least in part on the second signal, that a wiping motion has occurred with respect to the touch surface.

8. The system of claim 7, wherein the processing device suspends functional operation of the touch surface when the wiping motion has been determined to occur.

9. The system of claim 1, wherein the processing device is further to determine that a liquid is present on the touch surface following generation of the second signal, and wherein interpreting the second contact as a cleaning action with respect to the touch sensor comprises determining, based at least in part on the second signal, that a wiping motion has occurred with respect to the touch surface in conjunction with determining that the liquid is present on the touch surface following generation of the second signal.

10. The system of claim 9, wherein the processing device comprises a programmed processor to determine that the liquid is present on the touch surface based, at least in part, on non-uniformity of the signals generated by the plurality of sensors.

11. The system of claim 10, wherein the programmed processor is further to determine what tape of liquid is present on the touch surface based on the signals generated by the plurality of sensors and rate of evaporation information for a plurality of liquids.

12. The system of claim 1, wherein the plurality of sensors comprise capacitive sensors.

13. The system of claim 1, wherein the processing device is configured to determine a completeness of a cleaning of the touch surface by one or more of: determining whether a number of determined wiping motions exceeds a predefined number of determined wiping motions; determining an area of the touch surface covered by the determined wiping motions; determining whether a liquid was used based on the one or more signals; or determining what type of liquid was used based on the one or more signals and evaporation information.

14. The system of claim 13, further comprising an illumination component configured to illuminate the touch surface at one of various colors or intensities based on the determined completeness of touch surface cleaning.

15. The system of claim 13, further comprising a display device disposed beneath the touch surface and coupled to the processing device, wherein the processing device is configured to render a keyboard image on the display device and to visibly alter the keyboard image over time according to the completeness of touch surface cleaning.

16. A method of operation within a computing device having a touch-sensitive surface populated by an array of sensors, the method comprising:
generating first and second touch-indicative signals within a first sensor of the array in response to respective first and second user contacts with the touch-sensitive surface;
interpreting the first user contact as a user input with respect to an image rendered on a display of the computing device and revising the image rendered on the display in response;
interpreting the second user contact as a cleaning action with respect to the touch-sensitive surface based, at least in part, on the second touch-indicative signal and revising a value indicative of a contamination level of the touch-sensitive surface in response; and
suspending operation of the keyboard during the cleaning action.

17. The method of claim 16 wherein interpreting the first user contact as a user input with respect to an image rendered on the display of the computing device and revising the image in response comprises interpreting the first user contact as a keystroke with respect to a key of a keyboard depicted in the rendered image and displaying a corresponding alphanumeric character within the rendered image.

18. The method of claim 16 wherein interpreting the second user contact as a cleaning action with respect to the touch-sensitive surface comprises detecting, based at least in part on the second touch-indicative signal, a wiping of the touch-sensitive surface.

19. The method of claim 16 wherein revising the value indicative of the contamination level comprises revising the value to indicate a reduced contamination level, the method further comprising altering a visible aspect of a keyboard depicted in the display to reflect the reduced contamination level.

20. A computing device comprising:
a touch-sensitive surface populated by an array of sensors;
a display;
means for generating first and second touch-indicative signals within a first sensor of the array in response to respective first and second user contacts with the touch-sensitive surface;
means for interpreting the first user contact as a user input with respect to an image rendered on a display of the computing device and revising the image rendered on the display in response, and further for interpreting the second user contact as a wiping motion indicative of a cleaning action with respect to the touch-sensitive surface based, at least in part, on the second touch-indicative signal; and
a means for suspending operation of the touch-sensitive surface during the cleaning action.

* * * * *